United States Patent
Miller

(10) Patent No.: US 6,676,617 B1
(45) Date of Patent: Jan. 13, 2004

(54) BODY BRACE WITH ADJUSTABLE HINGE MECHANISM

(75) Inventor: John J. Miller, Boston, MA (US)

(73) Assignee: Boston Brace International, Inc., Avon, MA (US)

( * ) Notice: Subject to any disclaimer, the term of this patent is extended or adjusted under 35 U.S.C. 154(b) by 315 days.

(21) Appl. No.: 09/703,860

(22) Filed: Nov. 1, 2000

(51) Int. Cl.[7] .................................................. A61F 5/00
(52) U.S. Cl. ............................................ 602/5; 602/19
(58) Field of Search ................................ 602/5, 18, 19, 602/36; 2/44, 465, 467; 128/874, 875, 876

(56) References Cited

U.S. PATENT DOCUMENTS

| | | | | |
|---|---|---|---|---|
| 954,005 | A | * 4/1910 | Roth | 602/19 |
| 2,332,119 | A | * 10/1943 | Springer | 602/23 |
| 2,453,370 | A | * 11/1948 | Hittenberger | 602/19 |
| 2,828,737 | A | * 4/1958 | Hale | 602/19 |
| 3,171,407 | A | 3/1965 | Rogers | |
| 3,771,513 | A | * 11/1973 | Velazquez | 602/19 |
| 3,871,367 | A | 3/1975 | Miller | |
| 3,945,376 | A | * 3/1976 | Kuehnegger | 602/19 |
| 4,202,327 | A | 5/1980 | Glancy | |
| 4,577,346 | A | * 3/1986 | Hall | 2/2 |
| 4,833,730 | A | * 5/1989 | Nelson | 602/19 |
| 4,957,103 | A | 9/1990 | Young et al. | |
| 5,000,169 | A | 3/1991 | Swicegood et al. | |
| 5,010,881 | A | * 4/1991 | Boudreau | 602/19 |
| 5,012,798 | A | 5/1991 | Graf et al. | |
| 5,039,247 | A | 8/1991 | Young et al. | |
| 5,072,725 | A | 12/1991 | Miller | |
| 5,074,288 | A | * 12/1991 | Miller | 602/19 |
| 5,111,807 | A | 5/1992 | Spahn et al. | |
| 5,158,531 | A | 10/1992 | Zamosky | |
| 5,207,635 | A | * 5/1993 | Richards | 602/9 |
| 5,451,200 | A | * 9/1995 | LaBella | 602/19 |
| 5,474,523 | A | 12/1995 | Miller | |
| 5,503,621 | A | 4/1996 | Miller | |
| 5,620,412 | A | * 4/1997 | Modglin | 602/24 |
| 5,984,886 | A | 11/1999 | Miller | |
| 6,165,147 | A | * 12/2000 | Morrow | 602/19 |
| 2001/0008955 | A1 | * 7/2001 | Garth | 602/19 |

FOREIGN PATENT DOCUMENTS

| DE | 3622265 | * 7/1988 |
|---|---|---|

* cited by examiner

Primary Examiner—Michael A. Brown
(74) Attorney, Agent, or Firm—Lucash, Gesmer & Updegrove, LLP

(57) ABSTRACT

An adjustable, removable, interlocking iliac crest belt for a body brace is disclosed. The belt can be secured to the inside of a posterior portion of the body brace, and is secured about the patient's waist and upper hip region, engaging the iliac crests of the patient and providing additional pressure and stabilization force. Adjustable hook and loop fastening elements can be used to fasten the iliac crest belt. The belt is intended for use in body braces of the type for immobilizing or stabilizing a patient's spine in a post-surgical therapeutic application, or for treating abnormal spinal curvature, which brace may include body-conforming front and back shell elements molded from plastic, and adjustable strap elements affixed thereto for attaching the shells together around the torso of the patient with a selected compressive force.

20 Claims, 8 Drawing Sheets

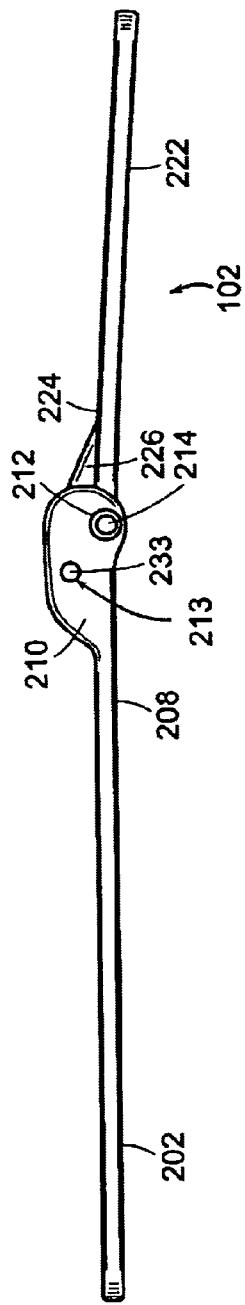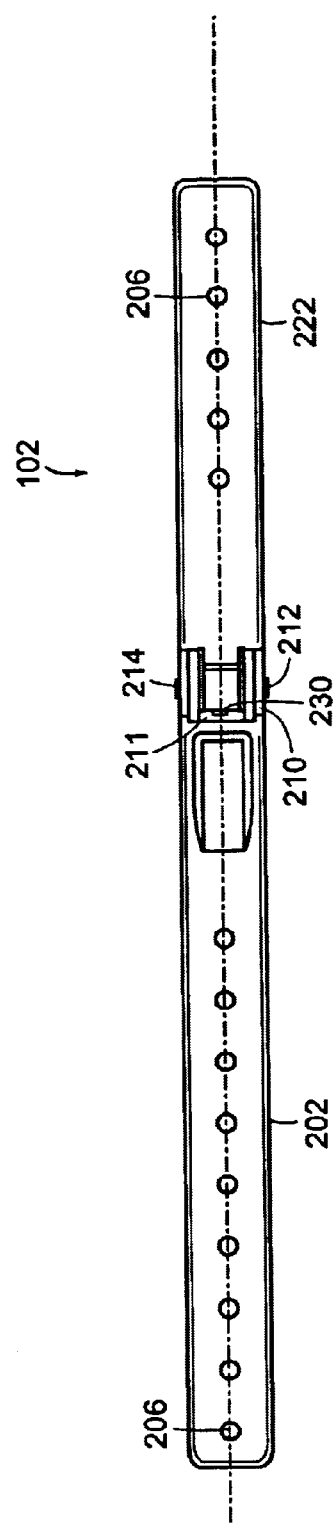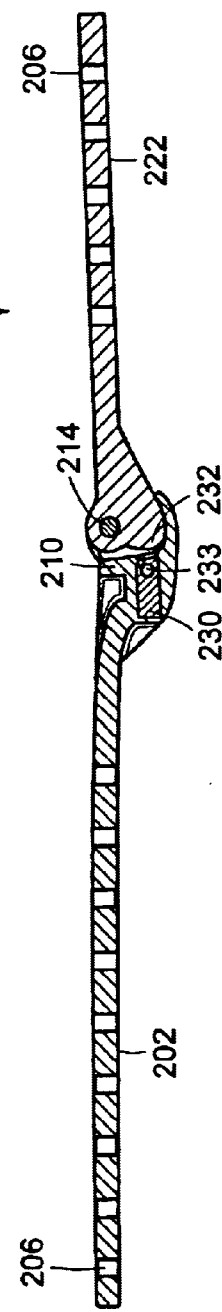
FIG. 5
FIG. 6
FIG. 7

BODY BRACE WITH ADJUSTABLE HINGE MECHANISM

FIELD OF THE INVENTION

The present invention relates generally to body braces, and, more particularly, relates to an adjustable, interlocking iliac crest belt assembly for use in such body braces.

BACKGROUND OF THE INVENTION

Body braces of the type designed to immobilize a patient's spine following lumbar or other spine surgery, or to treat scoliosis and other abnormal curvatures of the spine, such as hyperlordosis and hyperkyphosis, are known in the art.

By way of example, U.S. Pat. No. 5,503,621 to Miller, assigned to Boston Brace International, Inc., discloses a body brace for use in the treatment of scoliosis and other spinal abnormalities. The brace includes a bottom shell sized and shaped to be fitted around a patient's pelvis, a middle shell sized and shaped to be fitted around the patient's abdomen, and a top shell sized and shaped to be fitted around the back and the sides of the patient's rib cage. The top shell is made up of a left segment and a right segment. The middle shell is connected to the bottom shell by first and second lockable swivel mechanisms which provide for lateral, front and back, and rotational movement of the middle shell relative to the bottom shell. The left segment of the top shell is connected to the middle shell by a third lockable swivel mechanism which provides for lateral, front and back, and rotational movement of the left segment of the top shell relative to the middle shell, independent of the right segment of the top shell. The right segment of the top shell is connected to the middle section by a fourth lockable swivel mechanism which provides for lateral, front and back, and rotational movement of the right segment of the top shell relative to the middle shell independent of the left segment of the top shell. Releasable fasteners are attached to the top, middle and bottom shells to assist in holding the brace in place on the patient's pelvis, abdomen and rib cage, respectively.

Similarly, U.S. Pat. No. 5,474,523 to Miller, assigned to Boston Brace International, Inc., discloses a relatively rigid body brace for treating scoliosis in a patient while preventing hypokyphosis (flattening) in the patient's thoracic spine. The brace includes a shell shaped to surround the torso of a person in such a way as to correct scoliosis. The shell has an outer layer of hard plastic material and an inner layer of compressible plastic material bonded to the outer layer. The shell is preferably made from a single section and has a vertically extending split portion. To prevent hypokyphosis, the shell is shaped to define a kyphotic angle in the thoracic spine of approximately 20 to 25 degrees. The shell may additionally be shaped to define a lordotic angle in the lumbar spine of approximately 15 degrees to make the brace more comfortable to the wearer.

U.S. Pat. No. 3,871,367 to Miller, assigned to Boston Brace International, Inc., discloses a pelvic girdle comprising an outer layer of a substantially rigid plastic material and an inner layer of soft compressible plastic material bonded to the outer layer, the girdle being shaped to engage a person's pelvis and including an anterior and a vertically split posterior portion, the girdle having an upper anterior portion separated laterally from the remainder of the girdle and curving outwardly thereof, and connecting upper side portions on the girdle connecting the anterior and posterior portions thereof and including inwardly curved sections in both layers of the girdle for engaging the iliac crests of the wearer and which sections have appreciably thicker compressible inner layers thereon.

U.S. Pat. No. 4,202,327 to Glancy discloses a dynamic orthosis device which utilizes elastic forces to treat a patient who has scoliosis or other curvatures of the spine. The disclosed orthosis device includes first and second shell segments provided with a connecting arrangement for adjustably aligning the segments so as to encompass the torso of the patient. At least one pressure pad is pivotally mounted to one of the shell segments, and an elastic strap is adjustably secured to one of the shell segments so as to exert a predetermined force on the pressure pad. The elastic strap, pressure pad and shell segments cooperate to apply adjustable dynamic forces to correct abnormal curvatures of the patient's spine.

U.S. Pat. No. 5,012,798 to Graf et al discloses a dynamic orthosis device for the tridimensional reduction of scoliosis. The dynamic orthosis device includes two elastically deformable plastic hands joined at the anterior of the device to laterally enclose the thorax of the patient. The hands assembly is connected to a pelvic girdle by at least two lateral supports made of elastically deformable semi-rigid material. As the rear of the hands, which are not attached, are expanded outward due to the movement of the thorax of the patient, the lateral supports provide a torsional return stress which forces the hands to create a pressure on the body of the patient. This pressure is beneficial in reeducating the spine of the patient and thereby reduces scoliosis.

U.S. Pat. No 5,158,531 to Zamosky discloses a spinal orthosis which includes a continuous interior framework of ⅛" low density polyethylene sandwiched between layers of ¼" thick aliplast. The spinal orthosis also includes an anterior opening to provide cosmetic acceptability and independence of the user for placing on and removing the orthosis. A floating abdominal apron is provided to cover the anterior opening and the orthosis is devoid of joints and hinges to accomplish flexion and extension.

In a related area of development, support belts intended to maintain a preferred spinal orientation are also known in the art. Among these, U.S. Pat. No. 5,984,886 to Miller, assigned to Boston Brace International, discloses a support belt to be worn around the waist of a person. The support belt includes an elongated multi-layer strip having a center portion and a pair of ends. The elongated multi-layer strip is sized and shaped so as to encircle the waist of the person, with the center portion positioned against the back of the person and the pair of ends positioned against the front of the person, the pair of ends being releasably fastenable together to secure the support belt around the waist of the person. The center portion of the elongated multi-layer strip is shaped to define an angle of lordosis of approximately 15 degrees in the lumbar spinal region. A pair of inwardly curved sections, sized and shaped so as to urge against the iliac crests of the person wearing the support belt, are mounted on the multi-layer strip. The multi-layer strip may comprise a layer of rigid plastic and a pair of layers of a soft compressible plastic.

Other patents of interest include U.S. Pat. Nos. 5,111,807; 5,074,288; 5,072,725; 5,039,247; 5,000,169; 4,957,103; and 3,171,407.

The disclosure of each patent cited herein is incorporated herein by reference.

While the above-listed patents to Boston Brace International, Inc. and other manufacturers disclose useful bracing and support configurations, in many clinical situations, there is a need for additional sources of stabilization force and pressure to maintain proper spinal orientation. Thus, there is a need for additional stabilization and support elements for body braces that can provide such additional stabilization.

Accordingly, it is an object of the invention to provide improved stabilization elements for a body brace for post-surgical spinal stabilization and treatment of abnormal curvatures of the spine.

It is another object of the present invention to provide such stabilization elements for a body brace that can be used in the treatment of lateral, forward, backward, and rotational curvatures of both the upper and lower spine.

It is a further object of the invention to provide such stabilization elements having adjustable, lockable pressure elements.

It is yet another object of the invention to provide such a brace that is relatively simple to manufacture, assemble, and fit to a patient.

It is a further object of the present invention to provide a stabilization element for a body brace which can easily be placed on a patient and then removed when so desired.

SUMMARY OF THE INVENTION

These and other objects are attained by the invention, one aspect of which provides an adjustable, interlocking iliac crest belt for a body brace, for stabilizing a patient's spine in a post-surgical clinical setting, or for treating abnormal spinal curvature.

In accordance with this aspect of the invention, an adjustable, interlocking iliac crest belt can be affixed to the inside of a posterior portion of a body brace with rivets, screws or the like. The belt can be affixed to the back shell either in a removable or a non-removable manner. The belt can be tightened and locked about the patient's waist and upper hip region, engaging the patient's iliac crests and providing additional pressure and stabilization force when the brace is worn. Adjustable hook and loop fastening elements or the like can be located at the front portion of the belt, to permit fastening thereof. The belt thus forms an adjustable, interlocking iliac crest assembly.

In another aspect of the invention, the adjustable, interlocking iliac crest belt is utilized in a brace having semi-rigid, body-conforming front and back shell elements, which can be molded from well-known plastics such as HDPE. Adjustable strap and buckle elements can be affixed to the front and rear shells, respectively, for attaching the shells together around the torso of the patient with a selected compressive force. The strap and buckle elements can be affixed to the shells with rivets, screws or the like, and the straps secured with hook and loop fasteners or the like. The strap elements enable a given size of front and back shells to accommodate patients of various torso circumferences within a broad range.

In a further aspect of the invention, the brace can further include removable, compressible inner liner elements to pad the inner portions of the front and back shells, upper pressure plates, and iliac crest belt, thereby increasing comfort and stability.

Additional objects, features and advantages of the present invention will be set forth in part in the description which follows, and in part will be deducible from the description or may be learned by practice of the invention. In the following description, reference is made to the accompanying drawings which form a part thereof and which depict, by way of illustration particular embodiments and practices of the invention. Such embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is defined by the appended claims.

BRIEF DESCRIPTION OF THE DRAWINGS

The accompanying drawings, which are hereby incorporated into and constitute a part of this specification, illustrate embodiments of the invention. When considered with the description set forth herein, the drawings serve to explain the principles of the invention by way of example, but without limitation as to the scope of the invention, which is defined by the claims appended hereto. In the drawings, like reference numerals are used to represent like parts throughout the various views, and the following descriptions apply:

FIG. 5 is a side view of one of the hinge mechanisms of FIG. 4.

FIG. 6 is a top view of one of the hinge mechanisms of FIG. 4.

FIG. 7 is a cutaway side view of one of the hinge mechanisms of FIG. 4, showing the first and second hinge plates having a housing, abutment boss, hinge pin, multiple location holes, angle limiting (motion control) setscrew and locking screw.

GLOSSARY OF TERMS USED HEREIN

Lordosis/kyphosis: The normal human spine is substantially S-shaped, with two concavities (viewed from the posterior aspect), referred to as lordoses, and a convexity in the region of the shoulder blades, referred to as the kyphosis. The kyphosis forms the junction between the lordoses. A rounded back may be referred to as kyphotic posture. A flat or rearward-arched back may be referred to as lordotic posture.

Hyperlordosis: An abnormal accentuated arch in the lower back; a spinal deformity characterized by excessive extension, wherein the convexity of the curve is anterior.

Hyperkyphosis: Sometimes referred to as "rounded back"; a spinal deformity with accentuated forward angulation. In a normal adult human the thoracic spine upper back is gently rounded; hyperkyphosis commonly refers to excessive curvature of the thoracic spine (greater than approximately 25–30 degrees), as viewed from the side.

Scoliosis: A spinal deformity characterized by excessive lateral curvature and vertebral misalignment.

DETAILED DESCRIPTION OF THE INVENTION

Body Brace Details

Figure 1:
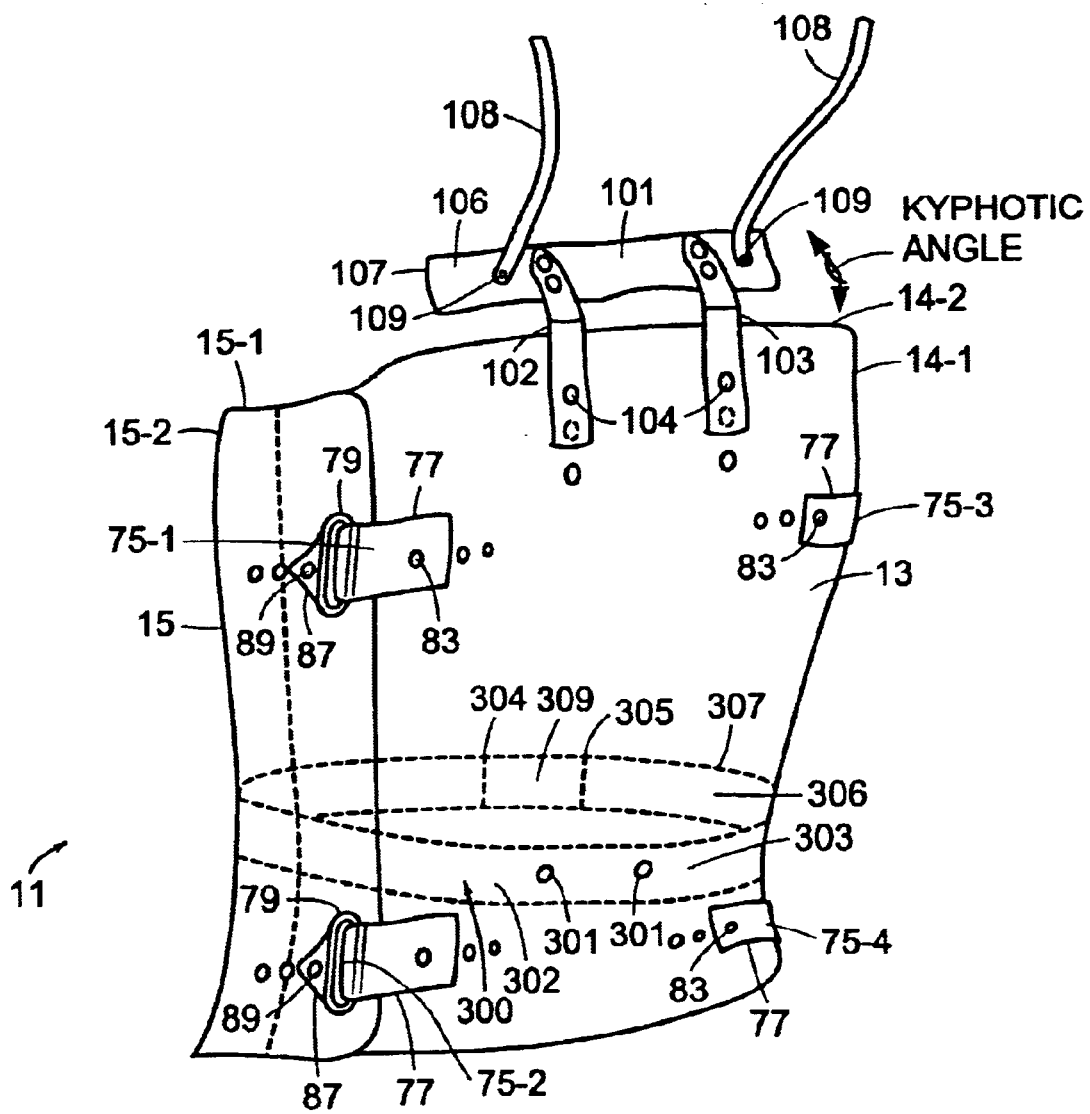
FIG. 1 is a rear perspective view of a body brace having an iliac crest belt constructed in accordance with the invention.
Figure 2A:
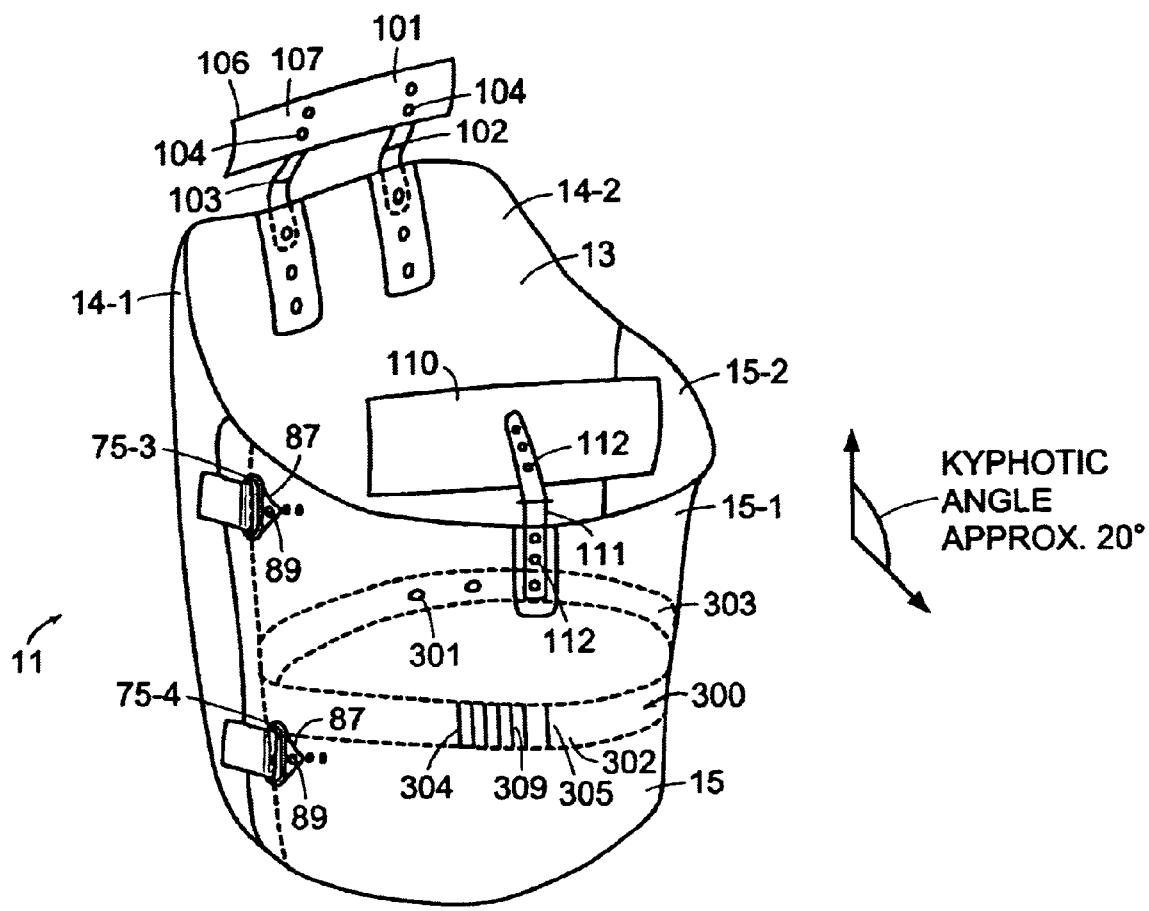
FIG. 2 is a front perspective view of the body brace shown in FIG. 1, showing the iliac crest belt and body brace of the embodiment of FIG. 1.
Figure 2B:
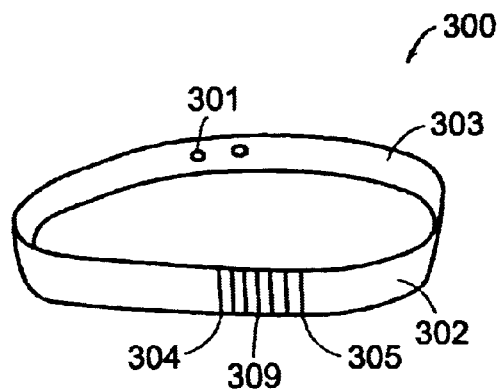
Figure 3:
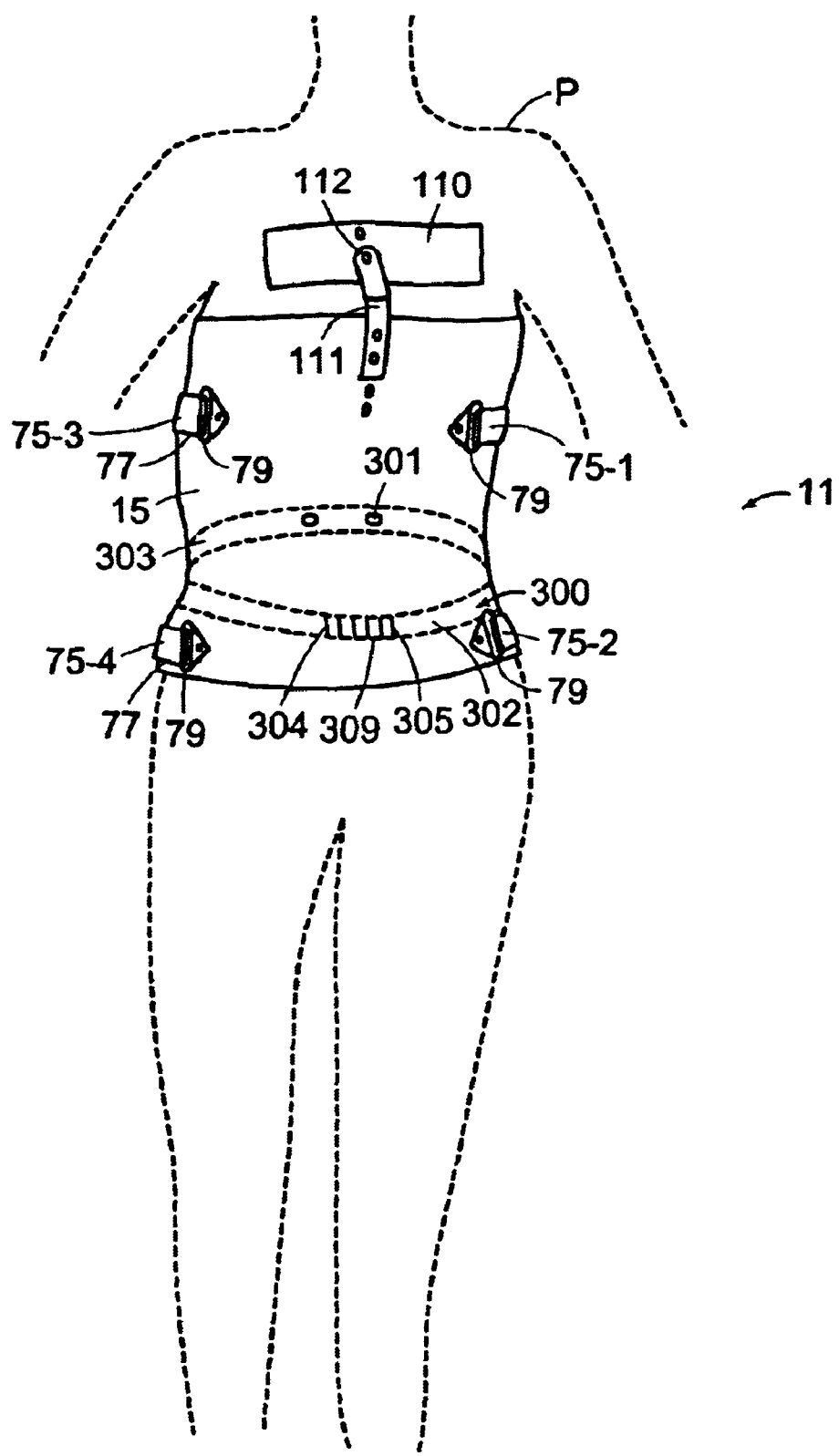
FIG. 3 is a front view of a patient wearing the body brace and iliac crest belt shown in FIG. 1.
Figure 4:
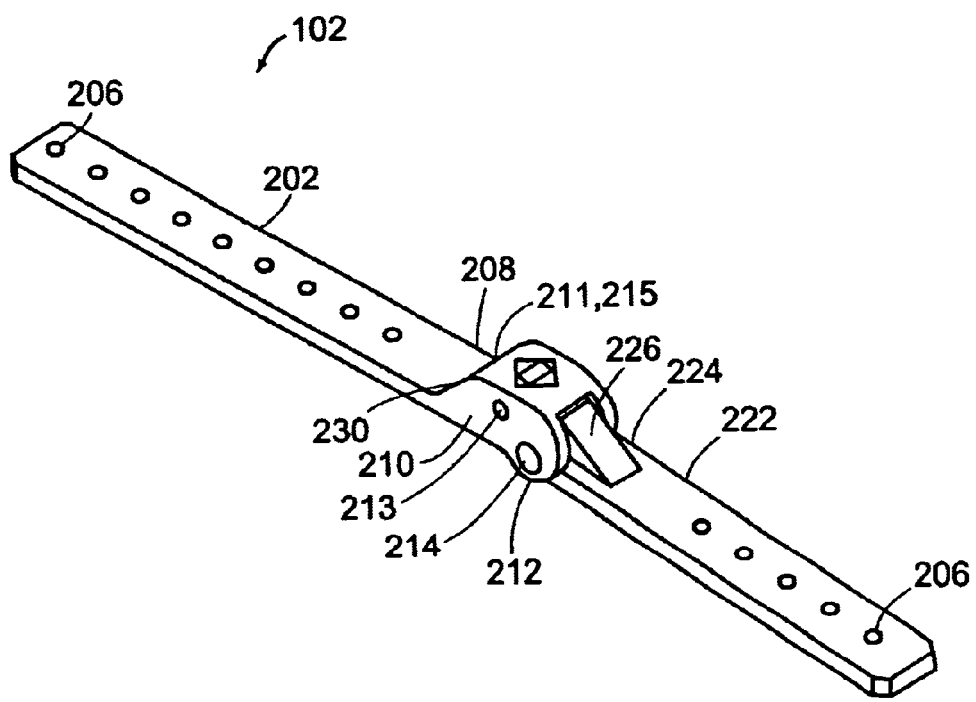
FIG. 4 is a perspective view of one of the hinge mechanisms used in the body brace of FIG. 1, showing the first and second hinge plates having a housing, abutment boss, hinge pin and multiple location holes.
Figure 8A:
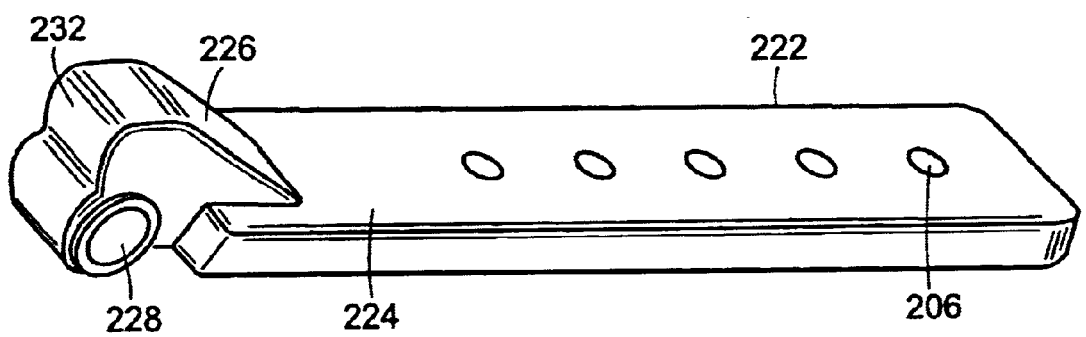
FIG. 8a is a perspective view of one of the two plates of the hinge mechanism shown in FIG. 4.
Figure 8B:
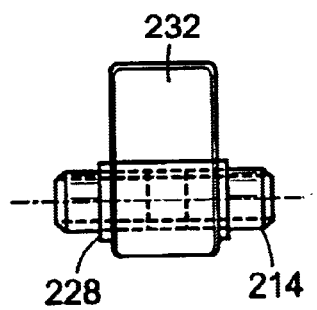
FIG. 8b is a front phantom view of detail of the hinge end (with hinge pin) of the plate shown in FIG. 8A.
Figure 9:
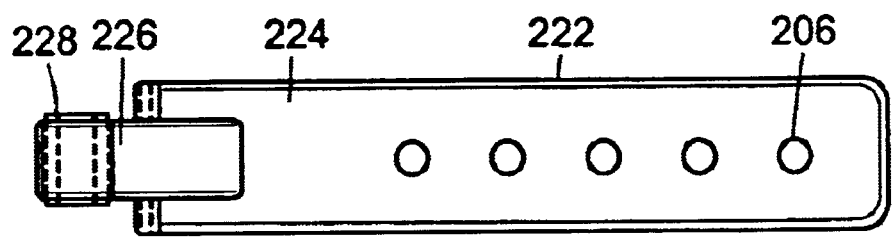
FIGS. 9–11 are top and side views of one of the two plates of the hinge mechanism shown in FIG. 4.
Figure 10:
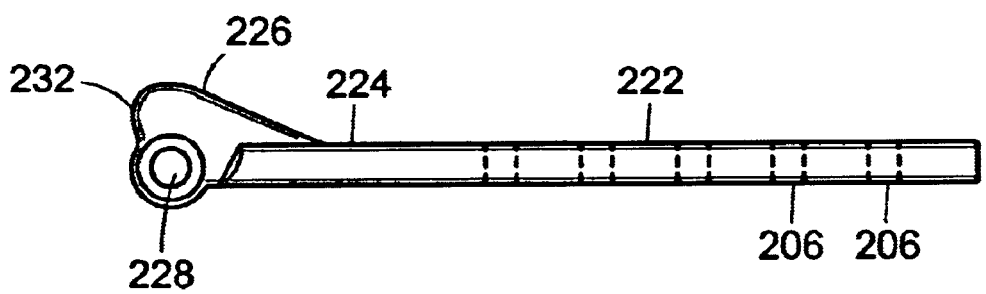
Figure 11:
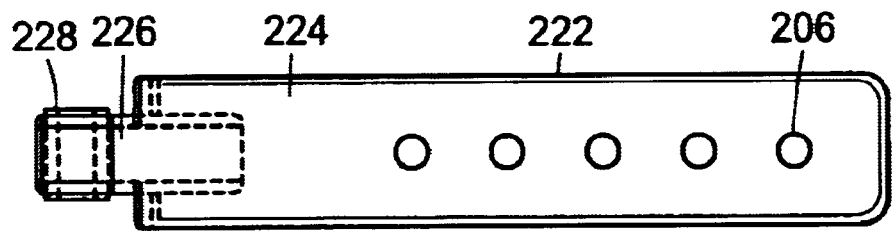
Figure 12C:
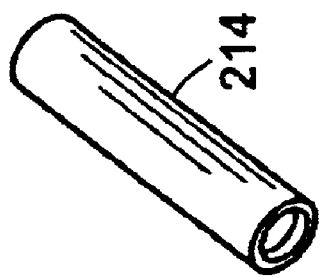
FIGS. 12a, 12b, 12c are side, end and perspective views, respectively, of the hinge pin of the hinge mechanism shown in FIG. 4.
Figure 12B:
Figure 12A:
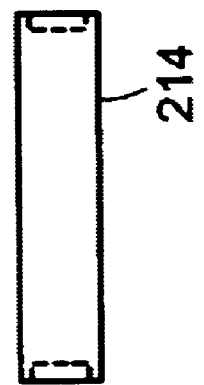

Referring now to the drawings, there is shown in FIGS. 1 and 2 a body brace utilizing an adjustable, interlocking, iliac crest constructed according to the teachings of the present invention, the body brace being represented generally by reference numeral 11. In FIG. 3, body brace 11 is shown on a patient P.

Body brace 11 includes a back shell 13 and a front shell 15.

Back shell 13 can be constructed of an outer layer 14-1 of a substantially rigid plastic material such as high density polyethylene (HDPE) or the like, and an inner liner layer 14-2 of a relatively soft, compressible foam material such as polyurethane or a similar material. A suitable liner material of closed-cell polyurethane foam is manufactured by Dicon Technologies, Inc. of Fairlawn, N.J.

Inner layer 14-2 can be removably attached to outer layer 14-1 with hook and loop fastener elements or other releasable fastener elements. Outer layer 14-1 may be about ⅛ to 3/16 inches thick and inner layer 14-2 may be about 3/16 to ¼ inches thick.

Similarly, front shell 15 can be constructed from an outer layer of substantially rigid plastic material and an inner layer of relatively soft compressible foam material and each of the same thicknesses as back shell 13.

Back shell 13 can be constructed in accordance with known molding techniques, and can be sized and shaped to fit and wrap about the patient's back and sides, forming a "lip" on either side of the patient that tends to retain and stabilize the brace and more evenly distribute binding forces. In addition, the shoulder area of back shell 13 can be made somewhat larger in circumference than the waist area, to accommodate the larger circumference of the patient's ribcage and upper body structure. It is contemplated that back shell 13 would be sized to be a relatively close fit to the patient's body. However, since it is constructed from semi-rigid material, back shell 13 can be flexed and expanded slightly, to facilitate slipping the shell on and off the patient.

Similarly, front shell 15 can be constructed in accordance with known molding techniques, and can be sized and shaped to fit and wrap about the patient's front and sides, forming a "lip" on either side of the patient that tends to retain and stabilize the brace and more evenly distribute binding forces.

It should be noted that shells 13, 15 may either be pre-formed into standard sizes, such as small, medium and large (such as for males, females and children) or may be cast and formed directly from the body of the patient.

In one embodiment of the invention, the front shell 15 overlaps the back shell 13 at the right and left sides of the patient and, as described hereinafter, is slipped onto the patient after fitting of the back shell 13.

In addition, the shoulder area of front shell 15 can be made somewhat larger in circumference than the waist area, to accommodate the larger circumference of the patient's ribcage and upper body structure. It is contemplated that back shell 13 would be sized to be a relatively close fit to the patient's body. However, since it is constructed from semi-rigid material, back shell 13 can be flexed and expanded slightly, to facilitate slipping the shell on and off the patient.

In the embodiment shown, four releasable fastener assemblies 75-1, 75-2, 75-3, 75-4 are used to connect and tighten front shell 15 to back shell 13 and assist in retaining the body brace around the patient's torso, with two fastener assemblies on the right side and two fastener assemblies on the left side of the body brace. Each fastener assembly 75-1, 75-2, 75-3, 75-4 includes a VELCRO or similar hook and loop fastener strap 77 and a buckle 79. Fastener straps 77 are attached to upper and lower locations on each of the right and left sides of back shell 13 by screws, rivets or similar fasteners 83. Multiple strap-attaching location holes can be provided at each strap-attaching region, to enable further customization via different strap positions and effective strap lengths. By way of example, this feature can be used to accommodate patients of different axial and radial (length and circumference) torso dimensions. Buckles 79 are attached to complementary attaching points on front shell 15 through chafes 87 by screws, rivets or similar fasteners 89.

Pressure Plates and Adjustable Hinges

Further stabilizing force can be applied, and a kyphotic angle (e.g., approximately 20 degrees) of the body brace can be established, by use of an upper posterior pressure plate 101 connected to back shell 13. Plate 101 can be substantially planar and rectangular, and approximately 3 by 8 by 0.25 inches, with the major axis of the plate being substantially horizontal and across the patient's back when fitted to the patient. In use, plate 101 presses upon the patient's thoracic region and is adjustably attached, at a selected angle and distance, to the upper portion of back shell 13 via hinge elements 102, 103 and screws 104. As described in further detail below, the hinge elements 102, 103 provide for adjustable length and kyphotic angle. The materials and methods used to construct upper posterior pressure plate 101 can be the same as those used in back shell 13, with a substantially semi-rigid "shell" 106 and a relatively compressible inner liner 107. In the embodiment shown, a pair of straps 108 are attached via rivets 109 to the upper posterior pressure plate. In use, after setting of hinge elements 102, 103, straps 108 can be wrapped around the patient's shoulders and secured with VELCRO or similar hook and loop fasteners, to provide additional stabilization force.

Additional stabilizing force can be applied, and a kyphotic or sternal angle (e.g., approximately 20 to 25 degrees) can be established, by a use of an upper chest pressure plate 110 connected to front shell 15. Plate 110 can have substantially the same shape, dimensions and materials as upper posterior plate 101. In use, plate 110 presses upon the patient's upper thorax and is adjustably attached, at a selected angle and height, to the upper portion of front shell 15 via hinge element 111 and screws 112. Hinge element 111 provides for adjustable height and angle in the manner described below.

Adjustable, Interlocking Iliac Crest Belt

Attached to the lower portion of the inside of the back shell 13, via fasteners 301, is a substantially semi-flexible iliac crest belt 300 (also referred to as an adjustable crest roll or inner locking crest). When in use, the iliac crest belt 300, which extends from around the back of the patient to the front of the patient, is tightened and releasably fastened about the patient's waist region so as to engage and urge against the patient's iliac crests (pelvic ridge) and thereby exert a tensile force on back shell 13. Belt 300 is thus an adjustable, interlocking assembly that enhances the stability and security of body brace 11. In one embodiment of the invention, fasteners 301 are rivets, so that the iliac crest belt 300 is fastened to back shell 13 in a non-releasable manner.

Iliac crest belt 300 includes an elongated strip of relatively rigid, i.e. non-flexible, material 302. Elongated strip of rigid material 302 is constructed of a low density material such as polyethylene to provide firm support and stabilizing force to the back of patient P; however, the rigid material could be materials other than polyethylene or other types of plastics.

Although iliac crest belt 300 is shown as comprising a single, elongated strip of substantially rigid material 302, the belt could be similarly constructed of a plurality of layers, one of the layers being of a substantially rigid material. Iliac crest belt 300 could also be constructed to include a relatively soft, compressible liner (constructed, for example, from the same material used to line the back and front shells 13, 15), which can be attached, removably or non-removably, by any suitable means to the inner surface of the belt, the liner serving to increase patient comfort.

Furthermore, iliac crest belt 300 could be constructed using one or more soft plastic layers whose configuration is maintained by one or more rigid stays on the inside, outside, or in between the soft plastic layers.

Elongated strip of rigid material 302 comprises a center portion 303, first end 304, a second end 305, an inner surface 306 and an outer surface 307. Center portion 303 and ends 304 and 305 can be integrally formed together as a single unit, such as through molding.

In the embodiment shown, elongated strip of rigid material 302 is sized and shaped so as to encircle the waist of person P with center portion 303 thereof positioned against the back of patient P and ends 304 and 305 positionable against the front of patient P. The elongated strip of material 302 is also sized and shaped so as to urge against the iliac crests of person P, thereby further securing and stabilizing the body brace. Where appropriate for enhanced patient fit, strip 302 can be relatively narrower around the back of the patient and relatively wider in the front.

The belt 300 further includes cooperating hook and loop elements 309 that together serve to releasably fasten ends 304 and 305 together in a well-understood manner, once the belt has been pulled tightly about the waist of patient P, thereby securing the belt 300 around the waist of patient P. Alternatively, the belt may include buckle and pin elements or other suitable attaching and securing elements to enable the belt to be tightened and secured.

It should be noted that belt 300 may either be preformed into standard sizes, such as small, medium and large (such as for males, females and children) or may be cast and formed directly from the body of the patient.

It will also be appreciated that additional pad elements, such as iliac crest pads, can be attached to the inner surface of the belt at appropriate positions adjacent the center portion of the belt, by an attachment means (not shown) such as hook and pile fasteners, adhesive, or other suitable means. Such iliac crest pads can improve the conformity of belt to the exact dimensions of the body of the wearer, and can be constructed, for example, of a soft compressible plastic material, such as 6 pound polyethylene foam.

Fitting of Body Brace to Patient

Body brace 11 may be fitted, assembled and used in the following manner. First, back shell 13 properly positioned around the patient's torso. Then the iliac crest belt 300 would be tightened to secure the back shell 13. The iliac crest belt 300 assists in initially securing the back shell 13 to the patient and setting the tightness of the back shell 13. Once the back shell 13 is secured, the front shell 15 would be properly positioned around the patient's torso, with the front shell 15 overlying the periphery of the rear shell 13 at the patient's right and left side rib cage, respectively. Once the back and front shells 13, 15 are properly positioned on the patient, the straps of the four fastener assemblies 75-1, 75-2, 75-3, 75-4 are secured with a selected tension, thereby fixing the position of shells 13, 15 on the patient. The tension on the four straps can be adjusted to secure the brace and meet the patient's needs, providing necessary stabilization force while accommodating the patient's torso circumference.

When the iliac crest belt is used, it will be seen that the front shell 15 and its liner element wrap around back shell 13 and liner; and the iliac crest belt 300 attaches to the back shell 13 with the liner of the back shell situated inside the belt, so that the relatively soft liner, rather than the inner surface of the iliac crest belt, bears against the patient, thus increasing patient comfort.

When upper pressure plates 110 and/or 101 are employed, they would be fitted to the front and back shells 15, 13, respectively, after the shells are secured to the patient, and the hinge mechanisms adjusted for length and angle, based on the patient's torso length and desired kyphotic angle, using the setscrews and the length adjusting holes in the hinge plates. Once the posterior pressure plate is fitted, the pressure plate straps can be placed around the patient's shoulders and secured to provide additional stabilization.

Body brace 11 can be removed from the patient when desired by loosening the fastener straps 75-1, 75-2, 75-3, 75-4, removing the front shell 15, loosening iliac crest belt 300 (if used) and removing back shell 13.

Hinge Details

FIGS. 4–12 illustrate detail of the construction of the hinges used in the body brace of FIG. 1. As noted elsewhere herein, the invention advantageously employs the same hinge construction in hinges 102, 103 and 111. As shown by way of example in FIGS. 4–12, hinge 102 is a two-piece clevis-type joint in which both maximum opening angle and arm length can be set and locked. Each hinge consists of first and second, generally flat, elongated hinge plates 202, 222, with each hinge plate having multiple, spaced-apart threaded holes 206 along its longitudinal axis.

Hinge plate 202 has, at its interacting hinge end 208, the receiving portion 210 of a clevis-type hinge, with a bore 212 therethrough, perpendicular to the longitudinal axis of the hinge plate 202, for receiving a roll-pin 214 that forms the pivot point of the hinge. The second plate 222 has, at its interacting hinge end 224, a complementary plug portion 226 sized and shaped to fit within the receiving portion 210 of the hinge, and with a bore 228 therethrough, perpendicular to the longitudinal axis of plate 222, for receiving the roll-pin 214, such that plug portion 226 of the hinge pivots about the roll-pin 214 when the hinge is assembled with the roll-pin 214 passing through both the receiving and plug portions 210, 226.

The receiving portion 210 also contains a first boss 211, parallel to the longitudinal axis of plate 202, with a threaded bore 215 therethrough for receiving a setscrew 230 for adjusting the maximum-open angle of the hinge. The plug portion 226 of the hinge also contains a boss 232 upon which the end of the setscrew 230 set in the boss 211 of the receiving portion will bear when the hinge is opened. By rotating the setscrew 230 and thereby changing its extension, the maximum-open angle of the hinge can be set. In this embodiment of the invention, the boss 211 on the receiving portion 210 of the hinge also contains a second threaded bore 213, perpendicular to and intersecting with the bore 215 of the first set-screw 230, for receiving a second set-screw 233 that can be used to prevent rotation of, and thereby lock, the first set-screw 230, such that the adjustment of the first set-screw 230 will be maintained.

The holes in the hinge plates can be, for example, 0.5 inches apart. The roll-pin 214 can be swaged into place at both ends, to prevent loss.

The hinge plates can be made of anodized aluminum, such as 6061-T6. The screws can be made of stainless steel, with the second setscrew having a nylon tip. The first setscrew, upon which the boss of the plug portion bears, can have, by way of example, a flattened, dog point. The setscrews are preferably recessed into the corresponding bosses, and are adapted to be adjustable only by use of hex keys or the like, such that while they are easily adjusted by a physician or orthotist, they are not easily tampered with by patients.

Length Adjustment

As shown in the detail portions of FIGS. 1 and 2, each of the pressure plates 101, 110 can have molded therein a channel for receiving one hinge plate of the above-described. In turn, each such channel can have two or more holes, of a diameter and spacing equal to those of the holes on the hinge plate (e.g., 0.5 inches on-center), so that screws can be passed through the holes of the pressure plate and into the threaded holes of the hinge plate. Since the hinge plate can also have a plurality of spaced-apart holes on it (e.g., between 5 and 8 holes), it will be appreciated that this feature permits the pressure plate to be slid back and forth along the hinge plate until a selected longitudinal position is obtained, depending upon the size and shape of the patient. Once that position is obtained, the screws can be inserted through the pressure plate and tightened into the hinge plate.

Similarly, the other hinge plate is fitted into a channel in the corresponding shell of the brace. In the embodiment shown in the drawings, one hinge is employed at the top of the front shell to adjust kyphotic angle. In the case of the upper portion of the back shell, two hinges are used to adjust kyphotic angle.

In this way, the effective length of each of the arms of each of the hinges can be adjusted, and thus both the angular and longitudinal (or radial) position of each of the pressure plates can be adjusted.

Advantages

It will thus be seen that the present invention provides numerous advantages over conventional brace designs, including the following:

1) an adjustable, interlocking iliac crest belt that utilizes lightweight, high-strength materials;
2) use of plastic materials for both weight reduction and convenience of use with X-ray and MRI equipment; and
3) relatively low profile that permits use of the iliac crest belt and brace under clothing.

The embodiments of the present invention described above are intended to be merely exemplary and those skilled in the art shall be able to make numerous variations and modifications to it without departing from the spirit of the present invention.

All such variations and modifications are intended to be within the scope of the present invention as defined in the appended claims.

What is claimed is:

1. A body brace comprising:
 a back shell sized and shaped to be fitted about a person's back,
 a front shell sized and shaped to be fitted about the person's front torso region,
 at least one fastening element for connecting the back shell to the front shell,
 at least a first pressure plate, connected to either the back shell or the front shell via at least a first adjustable hinge element, for applying pressure to a selected portion of either the back or the front torso region of the person,
 wherein the adjustable hinge element has at least first and second connection regions, the first connection region being connected to a portion of the first pressure plate, the second connection region being connected to a portion of one of the back or front shells,
 the adjustable hinge element connecting the first pressure plate to one of the back or front shells at a selected angle and at a selected longitudinal displacement therefrom.

2. The body brace of claim 1 wherein the first hinge element has a selectable maximum opening angle.

3. The body brace of claim 1 wherein the first hinge element has a selected effective length.

4. The body brace of claim 1 wherein the at least one fastening element includes a strap for connecting the back and front shells with a selected tension about the person.

5. The body brace of claim 4 wherein the at least one fastening element comprises a strap of hook and loop pile fasteners and a buckle.

6. The body brace of claim 1 wherein the at least first pressure plate is an upper front pressure plate connected via at least one of the adjustable hinge elements to an upper portion of the front shell at a selected angle, and with a selected longitudinal displacement, so as to contact the person's upper front torso region.

7. The body brace of claim 6 wherein the selected angle defines an angle of kyphosis.

8. The body brace of claim 1 wherein the at least first pressure plate is a upper back pressure plate connected via at least one of the adjustable hinge elements to an upper portion of the back shell at a selected angle, and with a selected longitudinal displacement, so as to contact the person's thoracic region.

9. The body brace of claim 1 wherein the first adjustable hinge element comprises:
 first and second hinge plates;
 a pivot for pivotally connecting the first and second hinge plates, the pivot defining a pivot point;
 a first contact surface associated with the first hinge plate,
 a second contact surface associated with the second hinge plate, for contacting the first contact surface when the hinge is opened to a selected angle, thereby defining a maximum opening angle of the hinge element;
 the second contact surface being defined by an adjustable element associated with the second hinge plate.

10. The body brace of claim 9 wherein:
 the first hinge plate has a raised portion adjacent the pivot, the raised portion defining the first contact surface,
 the second hinge plate has a raised portion adjacent the pivot, and
 the adjustable element is a first setscrew positioned in the raised portion of the second hinge plate, the position of the setscrew being adjustable to selectively move the second contact surface and thereby define a maximum opening angle of the hinge element.

11. The body brace of claim 10 wherein:
the second contact surface is an end surface of the first setscrew.

12. The body brace of claim 11 wherein the hinge element further comprises:
a locking element for locking the position of the first setscrew.

13. The body brace of claim 12 wherein the locking element is a second setscrew positioned in the raised portion of the second hinge plate so as to make contact with and lock the position of the first setscrew.

14. The body brace of claim 13 wherein:
the first hinge plate has a major axis;
the second hinge plate has a major axis;
the first hinge plate has at least two spaced-apart connection regions disposed along the major axis of the first hinge plate at different, selected longitudinal displacements from the pivot point, for connecting to the first pressure plate with a selected longitudinal displacement from the pivot point;
the second hinge plate has at least two spaced-apart connection regions disposed along the major axis of the second hinge plate at different, selected longitudinal displacements from the pivot point, for connecting to a portion of either the back or front shells with a selected longitudinal displacement from the pivot point.

15. The body brace of claim 14 wherein the spaced-apart connection regions comprise fastener-receiving regions for receiving a fastener.

16. The body brace of claim 15 wherein the fastener-receiving regions are holes.

17. The body brace of claim 16 wherein the holes are adapted to receive a rivet.

18. The body brace of claim 16 wherein the holes are adapted to receive a screw.

19. The body brace of claim 18 wherein the portion of the either back or front shells connected to the second connection region of the adjustable hinge element has a plurality of spaced-apart holes having a spacing corresponding to that of the holes disposed in the corresponding hinge plate, thereby defining a plurality of hinge-connecting regions on either of the back or front shells.

20. The body brace of claim 19 wherein the portion of the first pressure plate connected to the first connection region of the adjustable hinge element has a plurality of spaced-apart holes having a spacing corresponding to that of the holes disposed in the corresponding hinge plate, thereby defining a plurality of hinge-connecting regions on the first pressure plate.

* * * * *